United States Patent [19]
D'Amico et al.

[11] 4,150,027
[45] Apr. 17, 1979

[54] PROCESS FOR PREPARING 2-HYDROXYBENZOTHIAZOLE COMPOUNDS

[75] Inventors: John J. D'Amico, St. Louis; Ralph W. Fuhrhop, Webster Groves, both of Mo.

[73] Assignee: Monsanto Company, St. Louis, Mo.

[21] Appl. No.: 782,126

[22] Filed: Mar. 28, 1977

[51] Int. Cl.$^2$ .......................................... C07D 277/66
[52] U.S. Cl. ................................................. 260/304 B
[58] Field of Search ..................................... 260/304 B

[56] References Cited

U.S. PATENT DOCUMENTS 2,857,392  10/1958  Applegath et al. .............. 260/304 B
2,915,525  12/1959  Applegath et al. .............. 260/304 B

OTHER PUBLICATIONS

Kirk-Othmer, Encyclopedia of Chemical Technology, 2d. Ed., vol. 4, p. 432 (Wiley, 1964).

Primary Examiner—Donald G. Daus
Assistant Examiner—D. B. Springer
Attorney, Agent, or Firm—Richard H. Shear; Donald W. Peterson

[57] ABSTRACT

2-Hydroxybenzothiazole compounds are prepared by reacting o-aminobenzenethiol with carbonyl sulfide in the presence of a tertiary amine and a solvent.

5 Claims, No Drawings

PROCESS FOR PREPARING 2-HYDROXYBENZOTHIAZOLE COMPOUNDS The present invention relates to a process for preparing 2-hydroxybenzothiazole compounds having the formula

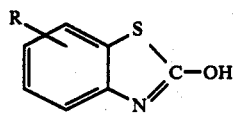

wherein R may be hydrogen, halogen, alkyl, nitro, $CF_3$, alkoxy or alkoxyalkyl. Compound I above may also exist in its tautomeric form

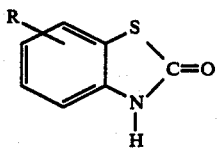

The 2-hydroxybenzothiazoles of the above formulae are useful as intermediates for the formation of 2-oxo-3-benzothiazoline plant growth regulants. Such plant growth regulants have been disclosed in U.S. Pat. No. 3,993,468.

It is known to prepare 2-hydroxybenzothiazole by a number of processes. U.S. Pat. No. 2,108,712 discloses the preparation of 2-hydroxybenzothiazoles by acidifying benzothiazole-2-sulfonic acid with hydrochloric acid. Also known is the preparation of 2-hydroxybenzothiazole by the hydrolysis of 2-chlorobenzothiazole. Other processes include the reaction of 2-clhorobenzothiazole with an aliphatic alcohol; the acidification of benzothiazole esters; and the reaction of o-aminobenzenethiol with $COCl_2$ in the presencce of toluene.

In accordance with the present invention, the 2-hydroxybenzothiazoles of the foregoing formulae may be prepared at atmospheric pressure by reacting o-aminobenzenethiol with carbonyl sulfide in the presence of a tertiary amine and a solvent. While the specific solvent to be utilized is not critical, it should be one in which both o-aminobenzenethiol and carbonyl sulfide are soluble. The determination of such solvents is well within the skill of the art and include chlorinated hydrocarbons such as chloroform and carbon tetrachloride, aliphatic alcohols, alkyl acetates, tetrahydrofuran, acetonitriles as well as others.

The specific tertiary amine to be used is also not highly critical. Tertiary amines which may be used include trialkylamines, pyridine, quinoline and the like.

The invention further contemplates the dissolving of o-aminobenzenethiol in a suitable solvent, after which a tertiary amine is added. Under normal circumstances, the temperature of the reaction mixture will rise due to the exothermic nature of the reaction. The reaction mixture may be allowed to cool to room temperature, or if desired, the mixture may be cooled externally to a temperature below room temperature, e.g. 0° C. While the carbonyl sulfide may be added to the reaction mixture before said mixture has cooled, it is preferable to allow said mixture to cool to at least room temperature before adding the carbonyl sulfide in order to obtain maximum absorption of carbonyl sulfide in the solvent. After adding said carbonyl sulfide, it is preferable to heat the reaction mixture to a temperature ranging from room temperature to the reflux temperature of the solvent to liberate $H_2S$ and drive the reaction to completion.

Generally, the amounts of reactants to be used is determined by the following equation

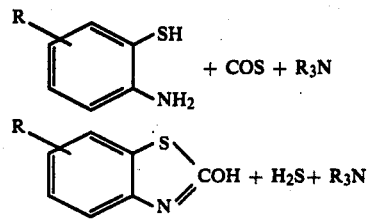

Thus, a stoichiometric equivalent of carbonyl sulfide and tertiary amine may be utilized. It is preferred, however, to use a slight excess of both. The amount of carbonyl sulfide to be added to the reaction mixture which contains o-amino-benzenethiol and tertiary amine is easily determined by the absorption of carbony sulfide. When the absorption of carbonyl sulfide into the solvent ceases, the addition of carbonyl sulfide is complete and may be stopped. The reaction is complete when all excess hydrogen sulfide has been liberated.

In accordance with the present invention, the following examples are presented. These examples are presented for purposes of illustration and are not intended to be a limitation as to the scope of the invention.

EXAMPLE 1

To a stirred solution containing 64.5 g (0.5 mol) of 97% o-aminobenzenethiol in 600 ml of tetrahydrofuran, 50.6 g (0.5 mol) of triethylamine was added in one portion. An exothermic reaction set in causing a temperature rise from 24° to 33° C. followed by the formation of a thick precipitate. After cooling the stirred slurry to 0° C., 38.9 g (0.55 mol) of 85% carbonyl sulfide (COS) was added at 0°–5° C. over a 40 to 50 minute period. External cooling was removed and the reaction mixture was stirred at 25°–30° C. for 24 to 72 hours. After stirring at these temperatures for 5 hours, a solution resulted. The stirred solution was heated at reflux for 2 hours. During this heated period hydrogen sulfide was liberated. The triethylamine and tetrahydrofuran were removed in vacuo at a maximum temperature of 80°–90° C. at 1–2 mm. (The recovered amine and solvent can be reused). To the cooled residue, 200 ml of water was added and stirred at 25°–30° C. for 15 minutes. The product was collected by filtration, washed with water until neutral to litmus and air-dried at 50° C. The results of three experiments are summarized by the table below.

| MP° C. Recryst[a] | % Yield | % Found[b] | | | |
|---|---|---|---|---|---|
| | | C | H | N | S |
| 140-1 | 97.7 | 55.71 | 3.36 | 9.22 | 21.35 |
| 140-1 | 96.6 | 55.44 | 3.43 | 9.17 | 21.30 |
| 140-1 | 96.6 | 55.60 | 3.37 | 9.27 | 21.18 |

[a]10 g recrystallized from 30 ml of toluene.
[b]Calc'd. for $C_7H_5NOS$: C, 55.61; H, 3.33; N, 9.26; S, 21.21.

EXAMPLE 2

To a stirred solution containing 64.5 g (0.5 mol) of 97% o-aminobenzenethiol in 200 to 600 ml of acetonitrile, 50.6 g (0.5 mol) of triethylamine was added in one portion. An exothermic reaction set in causing a temperature rise from 24 to about 40° C. followed by the formation of a precipitate. After cooling the stirred slurry to 0° C., 38.9 g (0.55 mol) of 85% COS was added at 0°–5° C. in 35 minutes. During this addition, a solution resulted after 10 to 35 minutes from the start of COS feed. External cooling was removed and the reaction mixture was stirred at 25°–30° C. for 24 hours. The stirred solution was heated at reflux for 2 hours. During this heating period, hydrogen sulfide was liberated. The triethylamine and acetonitrile were removed in vacuo at a maximum of 80°–90° C. at 1–2 mm. (The recovered solvent and amine can be reused in the next run). To the cooled residue, 200 ml of water was added and stirred at 25°–30° C. for 15 minutes. The product was collected by filtration, washed with water until neutral to litmus and air-dried at 50° C. The results of eight experiments are summarized by the table below.

| Acetonitrile ml. | MP° C. Recryst[a] | % Yield | % Found[b] | | | |
|---|---|---|---|---|---|---|
| | | | C | H | N | S |
| 200 | 140-1 | 91.5 | 55.49 | 3.35 | 9.24 | 21.22 |
| 200 | 140-1 | 91.3 | 55.66 | 3.35 | 9.25 | 21.12 |
| 200 | 141-2 | 91.3 | 55.66 | 3.37 | 9.26 | 21.27 |
| 400 | 140-1 | 91.3 | 55.62 | 3.39 | 9.25 | 21.15 |
| 400 | 141-2 | 91.3 | 55.67 | 3.36 | 9.28 | 21.15 |
| 500 | 140-1 | 96.6 | 55.55 | 3.37 | 9.29 | 21.30 |
| 600 | 140-1 | 96.6 | 55.47 | 3.35 | 9.26 | 21.21 |
| 600 | 141-2 | 96.6 | 55.62 | 3.39 | 9.29 | 21.26 |

[a]10 g recrystallized from 30 ml of toluene.
[b]Calc'd. for $C_7H_5NOS$: C, 55.62; H, 3.33; N, 9.26; S, 21.21.

EXAMPLE 3

To a stirred solution containing 64.5 g (0.5 mol) of 97% o-aminobenzenethiol in 200 or 600 ml of chloroform, 50.6 g (0.15 mol) of triethylamine was added in one portion. An exothermic reaction set in causing a temperature rise from 22 to about 50° C. The stirred solution was cooled to 0° C. and 38.9 g (0.55 mol) of 85% COS was added at 0°–5° C. in 35 to 40 minutes. The solution was stirred at 25°–30° C. for 24 hours and then heated at reflux for two hours. The $CHCl_3$ and $(C_2H_5)_3N$ were removed in vacuo at maximum temperature of 80°–90° C. at 1–2 mm. To the cooled residue, 200 ml of water was added and stirred at 25°–30° C. for 15 minutes. The product was collected by filtration, washed with water until neutral to litmus and air-dried at 50° C. The results of two experiments are summarized in the table below.

| $CHCl_3$ ml. | MP° C. Recryst[a] | % Yield | % Found[b] | | | |
|---|---|---|---|---|---|---|
| | | | C | H | N | S |
| 600 | 140-1 | 91.4 | 55.64 | 3.37 | 9.26 | 21.21 |
| 200 | 139-40 | 70.0 | 55.60 | 3.35 | 9.29 | 21.25 |

[a]10 g recrystallized from 30 ml of toluene.
[b]Calc'd. for $C_7H_5NOS$: C, 55.61; H, 3.33; N, 9.26; S, 21.21.

EXAMPLE 4

To a stirred solution containing 64.5 g (0.5 mol) of 97% o-aminobenzenethiol in 200 ml of methyl alcohol or 600 ml of methyl alcohol or isopropyl alcohol, 50.6 g (0.5 mol) of triethylamine was added in one portion. An exothermic reaction set in causing a temperature rise from 22° to about 45° C. After cooling the stirred solution of 0° C., 38.9 g (0.55 mol) of 85% COS was added to 0°–5° C. in 30 to 45 minutes. The remainder of the procedure is the same as specified in Example 3 above.

The results of three experiments are summarized in the table below.

| $CH_3OH$ ml. | $(CH_3)_2$ CHOH ml. | MP° C. Recryst[a] | % Yield | % Found[b] | | | |
|---|---|---|---|---|---|---|---|
| | | | | C | H | N | S |
| — | 600 | 140-1 | 81.0 | 55.57 | 3.35 | 9.24 | 21.13 |
| 600 | — | 140-1 | 88.0 | 55.58 | 3.36 | 9.25 | 21.17 |
| 200 | — | 140-1 | 82.3 | 55.56 | 3.36 | 9.27 | 21.18 |

[a]10 g recrystallized from 30 ml of toluene.
[b]Calc'd. for $C_7H_5NOS$: C, 55.61; H, 3.33; N, 9.26; S, 21.21.

EXAMPLE 5

To a stirred solution containing 64.5 g (0.5 mol) of 97% o-aminobenzenethiol in 600 ml of ethyl acetate, 50.6 g (0.5 mol) of triethylamine was added in one portion. An exothermic reaction set in causing a temperature rise from 24° to 32° C. followed by the formation of a precipitate. After cooling the stirred slurry to 0° C., 38.9 g (0.55 mol) of 85% COS was added at 0°–5° C. over a 50 minute period. External cooling was removed and the reaction mixture was stirred at 24°–30° C. for 24 hours. The turbid solution was heated at reflux for two hours and the triethylamine and ethyl acetate was removed in vacuo at maximum temperature of 80°–90° C. at 10–15 mm. Unreacted o-aminobenzenethiol (10 g) was removed by heating the residue at 99° C. at 1–2 mm. To the cooled residue, 200 ml of water was added, stirred at 25°–30° C. for 15 minutes, product collected by filtration, washed with water until neutral to litmus and air-dried at 50° C. The product, mp 129°–132° C., was obtained in 66% yield. After recrystallization from toluene, it melted at 140°–141° C.

Anal. Calc'd. for $C_7H_5NOS$: C, 55.61; H, 3.33; N, 9.26; S, 21.21 Found: C, 55.64; H, 3.33; N, 9.25; S, 21.10.

From the above examples, it can be seen that 2-hydroxybenzothiazole may be prepared in high yields. Further, by utilizing the process of the invention, the solvent and tertiary amine can be recycled.

Although this invention has been described with respect to specific modifications, the details thereof are not to be construed as limitations, for it will be apparent that various equivalents, changes and modifications may be resorted to without departing from the spirit and scope thereof and it is understood that such equivalent emobidments are intended to be included herein.

What is claimed is:

1. A process for the preparation of 2-hydroxybenzothiazole which comprises the steps of:
   (a) dissolving o-aminobenzenethiol in a solvent;
   (b) adding a tertiary amine to said solution;
   (c) cooling the resulting mixture to room temperature or below;
   (d) adding carbonyl sulfide to the cooled mixture; and then
   (e) heating the mixture containing carbonyl sulfide to obtain 2-hydroxybenzothiazole.

2. A process according to claim 1 wherein step (c) is performed by merely allowing the resulting mixture to cool.

3. A process according to claim 1 wherein external cooling means are used to perform step (c).

4. A process according to claim 1 wherein the mixture containing carbonyl sulfide is heated at a temperature ranging from room temperature to the reflux temperature of the solvent.

5. A process according to claim 4 wherein said mixture is heated to the reflux temperature of the solvent.

* * * * *